United States Patent [19]
Cho et al.

[11] Patent Number: 5,795,305
[45] Date of Patent: Aug. 18, 1998

[54] PROCESS AND DEVICE FOR NON-INVASIVE DETERMINATION OF GLUCOSE CONCENTRATION IN PARTS OF THE HUMAN BODY

[75] Inventors: Ok-Kyung Cho, Feldblumenweg 3, D-44267 Dortmund; Birgit Holzgreve, Dortmund, both of Germany

[73] Assignee: Ok-Kyung Cho, Germany

[21] Appl. No.: 662,340

[22] Filed: Jun. 12, 1996

Related U.S. Application Data

[63] Continuation-in-part of PCT/DE94/01475, Dec. 12, 1994.

[30]    Foreign Application Priority Data

Dec. 12, 1993 [DE] Germany .................. 43 42 105.9

[51] Int. Cl.$^6$ ............................................ A61B 5/04
[52] U.S. Cl. ................................. 600/549; 600/316
[58] Field of Search ............................ 128/736, 633, 128/637

[56]    References Cited

U.S. PATENT DOCUMENTS

| | | | |
|---|---|---|---|
| 5,050,612 | 9/1991 | Matsumura | 128/670 |
| 5,140,393 | 8/1992 | Hijikihigawa et al. | 357/25 |

FOREIGN PATENT DOCUMENTS

| | | |
|---|---|---|
| 0 420 177 | 4/1991 | European Pat. Off. . |
| 21 05 820 | 4/1972 | Germany . |
| 25 18 141 | 11/1976 | Germany . |

OTHER PUBLICATIONS

*Diabete & Metabolisme* (Paris) 1982, 8, 15–19 entitled "Facial and Sublingual Temperature Changes Following Intravenous Glucose Injection in Diabetics" by R.M. Hillson et al.

*Primary Examiner*—Max Hindenburg
*Attorney, Agent, or Firm*—Evenson, McKeown, Edwards & Lenahan, P.L.L.C.

[57]    ABSTRACT

A device is suitable both for determining with high accuracy and precision the temperature of the human body (surface temperature, temperature in layers next to the surface, temperature in bodily cavities, temperature gradient towards the inside of the body) and for detecting output units. Their measurement accuracy and precision is higher than that of conventional temperature and heat measurement devices. The device further allows temperature measurement and heat detection with a high spatial and temporal resolution. In addition, because of the high correlation discovered between the glucose concentration in human blood and body temperature and heat measured at certain points of the body, the device is extraordinarily suitable for non-invasively and even contactlessly determining the glucose concentration in parts of the human body, in particular the human blood.

36 Claims, 2 Drawing Sheets

$c2 = 23.92 + c1 * 0.8043$ c1: INVASIVE METHOD
   HEXOKINASE METHOD c2: NON-INVASIVE METHOD

N = 175;           N: NUMBER OF PERSONS
R = 0.9129         R: COEFFICIENT OF CORRELATION
$\bar{c}$ = 171 mg/dl   $\bar{c}$: ARITHMETIC MEAN OF CONCENTRATIONS $c_2$
sR(c) = 26 mg/dl;  sR(c): SUM OF SQUARES DUE TO ERROR
ERROR RATE: 15%    $(sR(c)/\bar{c} \times 100)$

PROCESS AND DEVICE FOR NON-INVASIVE DETERMINATION OF GLUCOSE CONCENTRATION IN PARTS OF THE HUMAN BODY

CROSS-REFERENCE TO RELATED APPLICATIONS

This application is a continuation-in-Part of PCT application Ser. No. PCT/DE94/01475 filed on Dec. 12, 1994.

BACKGROUND OF THE INVENTION

1. Technical Field

The present invention relates to an electronic device for determining with high accuracy and precision the temperature of the human body and for detecting the heat of the human body, thus, permitting non-invasive determination of glucose concentration in parts of the human body, in particular in human blood.

2. State of the Art

1. Physical Background

The thermodynamic temperature, long called absolute temperature, is a value characterizing the overall thermodynamics occurring in the relationship between state variables derived from the second main theorem of thermodynamics. On the basis of the second theorem, the thermodynamic temperature is a solely positive value having by nature a defined zero point. For this reason, it suffices to define the temperature unit as a specific part of an unequivocally determined thermodynamic temperature. Used for this purpose is, according to a decision by the 10th General Conference on Measurement and Weight in 1954, the water triple point, to which the thermodynamic temperature $T_{tr}=273.16K$ is assigned by definition. Thus, the temperature unit Kelvin is defined by $$1K = T_{tr}/273.16.$$

Frequently employed instead of the parameter T is a special difference value between thermodynamic temperatures called Celsius temperature t with $$t = T - T_0 = T - 273.15 K.$$

The unit of Celsius temperature is the degree Celsius (°C.); it has the same value as Kelvin. The zero point of Celsius temperature is the thermodynamic, temperature $T_o=273.15K$; it lies exactly 0.01K below the temperature of the water triple point.

2. Measurement of Temperature

Of the very numerous possible temperature measurement devices, the principles most commonly used today in the best known conventional thermometers are presented in the following:

2.1 Expansion thermometers are contact thermometers, which have to come in mechanical contact with the object to be measured. They utilize the thermal expansion of a fluid (gas or liquid) or a solid material for measuring the temperature.

2.1.1 of the glass liquid thermometers, the best known and the most commonly used measuring devices are mercury-filled thermometers. They are easy to handle and require no auxiliary devices. With them, measurement accuracy between −39° C. and 630° C. can be achieved, which in general only resistance thermometers can surpass but at great expense and effort. With a good glass mercury thermometer, measurement uncertainty of 5 mK can be achieved in the 100° C. to 110° C. range. Advantageous are the narrow tolerances with which these thermometers can be produced (DIN 12 771). Disadvantageous is the large volume of the thermometer vessel resulting in major display delay. A glass liquid thermometer is unable to keep, up with rapid changes in temperature. It is also not suitable for measuring spatially non-homogeneous temperature fields. Its rigid design, with only few deviations from the basic form, greatly limits its use in sites that are difficult to reach.

Other expansion thermometers include: spring type liquid thermometers, spring type gas thermometers, and metal expansion thermometers. Their measurement uncertainties are in the 1% to 3% measuring range.

2.2 In resistance thermometers, the temperature dependency changes in the electrical resistance are utilized as a measure of temperature. Preferred materials for such thermometers include metals and semiconductors, whose changes in resistance are big and reproducible. The greatest accuracy in thermometry is obtained with platinum, ferric-rhodium and germanium resistance thermometers section-wise in the 1K to 1340K range.

2.2.1 The great measurement stability in the 10K to 1340K application range makes platinum resistance thermometers one of the most commonly employed temperature measuring devices. Platinum resistance thermometers have been meanwhile developed whose measurement uncertainty lies at the gold point of 0.01K.

2.2.2 Semiconductors are also increasingly used as measurement resistors for resistance thermometers. Its resistance changes substantially more with temperature than the resistance of metals. In most semiconductors, the temperature coefficient of the electrical resistance is negative (such as a thermistor, also called "NTC resistance" or in short "NTC" (negative temperature coefficient). Posistors have a positive temperature coefficient in a limited range.

2.3 Thermoelements are the most commonly employed electric thermometers in the 1K to 3000K temperature range. Although their measurement uncertainty is larger than the measurement uncertainty of resistance thermometers, the thermoelements are, however, much easier to produce, have small spatial expansion, have a short response time and are especially suited for measuring temperature differences. Voltage compensators or high impedance voltmeters are used for measuring thermoelectric voltage.

2.4 In a narrow temperature range, in which vapor pressure can be easily measured, fluids with low boiling points, e.g. helium, hydrogen, oxygen and nitrogen, are gases suitable for use with a vapor pressure thermometer. This thermometer is often employed in Kryo technology. In the range of very deep temperature (0.5 K to 5.2K), the helium vapor pressure thermometer is among the temperature devices with a very high reproducibility.

2.5 Fundamentally, a temperature measuring process can be based on any known relationship between a material property and the temperature. In addition to the previously described processes, for instance, the temperature dependency of sound velocity in solid bodies up to very high temperature, the anistropy of gamma radiation for T<80 mK, the quadrupolar nuclear resonance for 300 K>T>20K etc., can-be utilized for temperature measurement.

3. Physiological Background 3.1 Biological rhythm of glucose in the blood

Close-mesh blood glucose profiles, both day and night, of normal as well as ill people show common characteristics such as rising in the evening, dropping at night, rising again in the early morning, despite different external factors such as age, nutrition, illness, etc. These common characteristics seem to reflect endogenic and vegetative periodicity. Such periodic fluctuations are known as circadian rhythms. These are understood to be biological rhythms having a periodic length of approximately 24 hours. This biological rhythm continues even if two important ambient periodicities such as light and ambient temperature remain constant.

In multiple cell organisms, both the functions of the overall organism and those of the individual organs and cells are subject to rhythms which are in a specific phase relationship to each other and to the ambient periodicity and are called "circadian organization". For example, glycogen, glycogen-synthetase and phosphorylase and the corresponding glucose concentrations in the blood indicate a distinct parallel rhythm.

In humans, the vegetative functions, such as pulse, blood pressure, blood circulation, respiration, body temperature, etc. are also subject to circadian periodicity. The activity phases, have a duration e.g., with individual fluctuations, lasting from 0800–1200 and 1600–1900 o'clock. During this time, metabolism is catabolic and, for instance, body temperature, blood pressure and glucose concentration in the blood are raised. The human is ready to work.

On the other hand, the vagotonic recuperation phases lie between 1300–1500 and 2200–0600 o'clock. The above-mentioned parameters are low, hence the human is ready to sleep. These phases are subject to temporal shifts, which can be classified as early risers and late risers.

The paper by R. M. Hillson et al., "Facial and Sublingual temperature changes following intravenous glucose injection in diabetics", pp. 15–19, Diabete & Metabolisme, vol. 8, 1992 Paris, describes an experiment run with 61 diabetics, who were injected with certain amounts of glucose. Within two minutes following injection, certain changes, for example reddening of the cheeks, a subjective sense of heat, etc., were observed among the test participants. Their temperatures were measured under the tongue (sublingual) and on the cheek. It was observed that immediately following the injection, there was a rise in the cheek temperature with a simultaneous drop in the sublingual temperature.

Furthermore, German Patent document DE 2 105 820 AJ describes a diagnostic instrument responding to infrared radiation. The purpose of the device is to locate veins under the skin. The measurement device utilizes the fact that there is a difference in temperature between the veins that blood flows through and the surrounding tissue. Uncooled bolometers of various designs are employed as detectors in this reference.

SUMMARY OF THE INVENTION

The object of the present invention is to build a device for the purpose of measuring the temperature of the human body (e.g. the surface temperature, the temperature of layers close to the surface, in body cavities as well as temperature gradients, etc.) and detecting the heat of the human body, the measuring accuracy and precision of which surpasses the measuring accuracy and precision of conventional devices for measuring temperature and detecting heat. Furthermore, the object of the present invention is, i.a., to permit the measuring of temperature and detecting of heat with a high spatial and temporal resolution.

The present invention, moreover, is based on the striking discovery that there is major correlation between the circadian fluctuation of the glucose concentration in the human blood and the circadian periodicity of the body temperature measured at certain suitable points such as the fingertip and the detected heat. The body temperature and the body heat can therefore be used to determine glucose in the blood.

Accordingly, the present invention describes a process which permits accurate determination of the glucose concentration in the blood of the human body via highly precise measurement of the temperature and detection of the heat of the body. Additionally, this can be done noninvasively, i.e. in a manner that does no injury to the body and, furthermore, in a contactless manner. Thus, removal of capillary blood from the finger tip or the ear lap as is required in conventional processes for determining glucose in the blood is eliminated.

A suitable mathematic evaluation algorithm permits allocation of the measured, detected, and processed temperature and heat data to the glucose concentrations. Influences and disturbances due to environmental conditions (such as ambient temperature, humidity, air pressure, etc.), nutritional intake (quality, time), health and physical and psychological states are individually compensated for in the evaluation algorithm by suitable auxiliary functions.

Other objects, advantages and novel features of the present invention will become apparent from the following detailed description of the invention when considered in conjunction with the accompanying drawings.

DESCRIPTION OF A PREFERRED EMBODIMENT

An element of the present invention is that at least one, as such, known miniaturized thermistor (NTC resistance) is utilized to measure the temperature. The NTC resistance is located in a suitable holding device made of a material possessing a thermal conductivity which is as low as possible and forming therewith one unit, the so-called sensor head. Various geometrical shapes are possible for the holding device. However, the holding device either accommodates the NTC in a hollow space in a manner permitting contactless measurement of the heat radiating from the object to be measured or it offers the NTC support at a suitable site for (contact) measurement of the heat radiating from the object to be measured by means of thermal conductivity. Furthermore, the holding device serves to protect the NTC against destruction and soiling.

It is noted that there are very many heat-generating processes of a biochemical and biophysical nature occurring in the human body. These processes, which vary according to origin and source, can be considered as different sources of heat. Each of these sources of heat generates its own characteristic thermal spectrum, i.e. thermal radiation having certain frequency ranges.

Due to the varying nature of the generating sources, the heat generated by the body has a specific, characteristic heat spectrum. In the case of thermal conductivity through a medium, one works frequency-selectively by utilizing dispersion within the medium. In the case of thermal radiation, one determines certain frequency ranges using suitable filters. These techniques are sufficiently familiar to those skilled in the art.

The measuring principle calls for either, e.g., two successive measurements (sequential) with an NTC or simultaneous measurement (simultaneous) with, e.g., two NTCs. Therefore, a preferred form of construction contains at least two NTCs, an especially preferred form of construction of the invented device contains at least 3 NTCs. In the latter variant, either two offset NTCs located in a hollow space which is open at the top are used to measure heat radiation, whereas the third NTC located on the surface of the holding device or in its wall is used to measure thermal conductivity, or one NTC located in a hollow space which is open at the top is used to measure heat radiation, whereas two offset NTCs located on the surface of the holding device or in its wall are used to measure thermal conductivity.

Figure 2A:
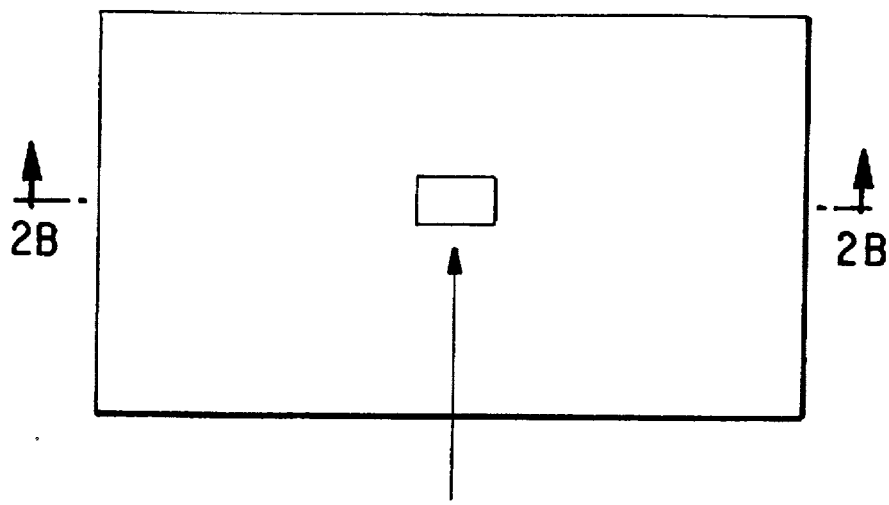
FIGS. 2A and 2B are a plane view and a cross-section view, respectively, of a sensor head according to the invention.

In a preferred embodiment, the sensor head (FIGS. 2A and 2B) is made of wood or a similar material. In an especially preferred design, the sensor head consists of a hollow body which is tightly closed when the opening touches the object to be measured such as a fingertip, or by insertion of the object to be measured into the hollow cavity. In another preferred design, the hollow body contains at least one opening for the purpose of cooling. With this arrangement, measurement can occur in atmospheric pressure and in protective gas. Moreover, the above-mentioned interior space can also be evacuated. NTCs (with quasi zero-mass leads) for contact and contactless measurement are therefore located in a vacuum. In this way, obvious disturbing influences can be minimized.

Technically, the sensor can be designed in such a manner that, on the one hand, a part of its surface touches the finger, while on the other hand, e.g., a recess in the surface permits the radiation to travel over a certain, probably defined, distance through free space in order to subsequently impinge upon the correspondingly designed point of the sensor.

A special, electronic circuit converts analog measured values having a resolution of 24 bits into digital data permitting temperature measurement having resolutions of <10–4K. The issuing, i.e., radiated heat, can also be thermoanalytically detected, i.e., selected wavelengthwise or frequency wise. A microcomputer (onechip) containing the evaluation algorithm compares the measured data with the stored calibration functions and allocates certain temperature values to concentration values. The programming of the microcomputer in order to accomplish the functions performed by the evaluation algorithm is well within the scope of one of ordinary skill in the art.

A digital/analog converter transmits the processed data to a suitable display (liquid crystal display, monitor, etc.) which indicates the determined glucose concentration as a numerical value (selectively in mg/dl or mol/l).

Basic Description of the Mathematical Evaluation Algorithm

To start with, both the device and its individual components are calibrated. Then, the relationship between the detected measured values and the glucose concentrations is established in the form of a calibration function and an analysis function: a measurement process (sequential or simultaneous; see above) according to the measurement principle yields two measured values $X_{1i}$ and $X_{2i}$. In addition, the glucose concentration in the blood is determined in a known, conventional manner (invasive). The measurement processes therefore yield 2 measured values $X_{ni}$ and n glucose concentrations $c_n$. Highly correlated relationships are established between the concentrations $c_n$ and the respective processed $X_{1i}$ and $X_{2i}$. Two calibration functions are subsequently yielded.

With respect to the calibration, first a correlation between the measured value Xi and the concentration of the glucose of ci is described in the form of a calibration response analysis function: For example $X_i = f(c_i)$ bzw. $c_i = f{-1}(X_i)$, respectively, where $X_i = f(Z_i, Z_2, \ldots, Z_j)$ i.

Z1; background of Z

Z2 ; reference value to Z

Z3-j; the measured data corresponding to temperature, heat etc.

c; glucose concentration derived from the reference method considered to be a true value.

Additionally, one or more parallel functions can be evaluated:

$$X1l = f\ (c1i)$$
$$X2l = f\ (c2l)$$
$$\vdots$$
etc.

In case the values c1 and c2 are within a given tolerance interval, then c1, c2 or the arithmetically, geometrically or otherwise evaluated mean values of c1 and c2 are presented as the result of the analysis.

It is advisable to produce one or more auxiliary help functions:

$$X1i = f\ (X2i),$$
$$X2i = f\ (X3i)$$
$$\vdots$$
etc.

The auxiliary help functions prove very relevant to realize an analysis method, which is without matrix effects and independent of any individual person.

Figure 1:
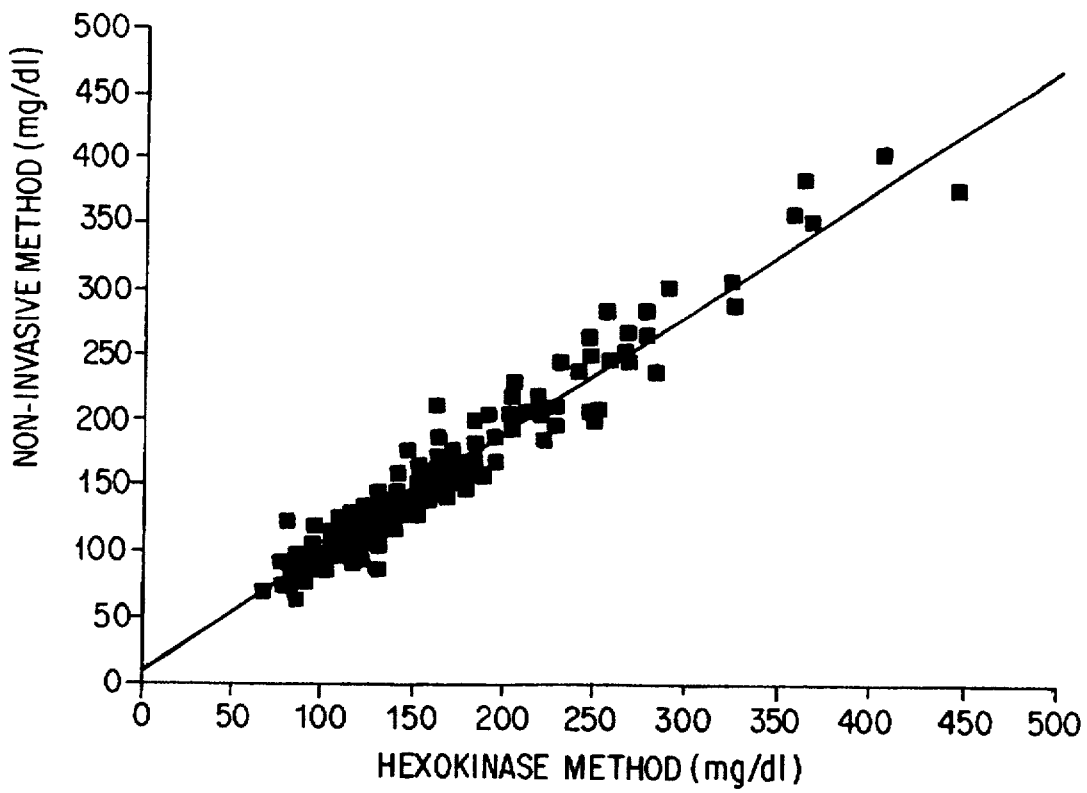
FIG. 1 is a graph showing an analytical performance including data illustrating the correlation between the hexokinase method and the non-invasive method according to the invention.
Figure 2B:
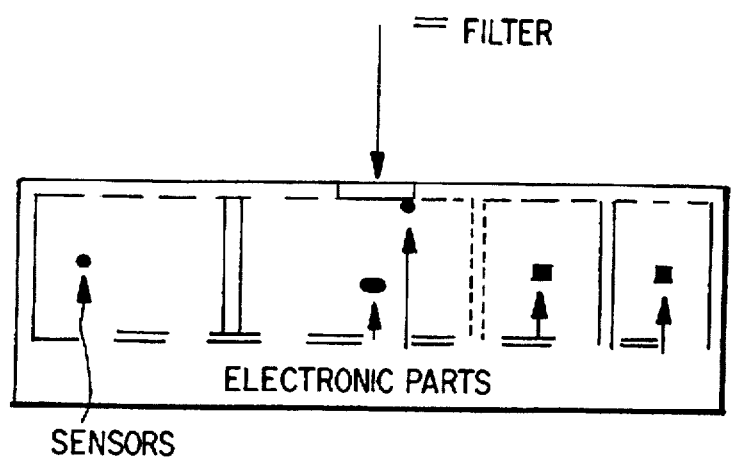

Moreover, one (or more) auxiliary functions are set up by, e.g., establishing the relationship of the measured values $X_1$ and $X_2$ to each other, taking into consideration the human body's biochemical and biological processes. The auxiliary function proves to be absolutely necessary, in particular, in order to be able to develop a matrix effect free analysis process, i.e., one that is patient-independent. FIG. 1 is a graph showing an analytical performance including data illustrating the correlation between the hexokinase method and the non-invasive method according to the invention. FIGS. 2 and 2B are a plane view and a cross-section view of a sensor head according to the invention as described above.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A process for non-invasive determination of glucose concentrations in parts of the human body, the method comprising the steps of:

measuring predefined spatially and temporally resolved temperatures on a surface of the body, and a thermal output from the body using highly accurate, at least one of contacting and contactless temperature measurement processes;

allocating the spatially and temporally resolved temperatures and the thermal output using their functional relationship via a mathematical algorithm; and providing the allocated spatially and temporally resolved temperatures and the thermal outputs to an output unit which displays information depicting glucose concentrations in parts of the human body.

2. A process according to claim 1, wherein the glucose concentration in human blood is determined.

3. A process according to claims 1, wherein said mathematical algorithm is selectively controlled in one of a patient-dependent and patient-independent manner.

4. A process according to claims 1, further comprising the step of determining analyses results for a patient-independent control which is matrix effect free with the aid of at least one principle function and at least one auxiliary function.

5. A process according to claim 4, further comprising the step of establishing mathematical relationships between at least two measured temperatures and the detected thermal output for the patient-independent evaluation processes.

6. A process according to claim 1, wherein said mathematical algorithm is a linear regression process either having an independent variable or having an independent variable of the first or higher order derived from measured temperatures and the detected thermal output.

7. A process according to claim 1, wherein said mathematical algorithm is a linear regression process either having two or more independent variables or having two or more variables of the first or higher order derived from measured temperatures and the detected thermal output.

8. A process according to claim 1, wherein a difference in temperature and a difference in heat, dependent on the respective patient and his/her health, between two independently, simultaneously or time offset, at least one of spatially and temporally resolved measured temperatures and detected thermal output is determined via at least one auxiliary function and is utilized as an individual compensation factor.

9. A process according to claim 1, wherein different sources of the thermal output radiating from the human body are separated by one of thermoanalytically, according to wavelength, and according to frequency.

10. A device for non-invasive determination of glucose concentrations in parts of the human body using highly accurate temperature measurement and heat detection, comprising:

at least one sensor head containing at least one NTC resistance for detecting the heat conducted and radiated from the body;

an associated electronic control unit for converting analog measured values into digital data, a measurement unit for measuring the conducted and radiated heat from the body detected by the at least one NTC resistance, an evaluation unit for storing an evaluation algorithm; and an output unit coupled to the at least one sensor head for displaying information depicting glucose concentrations in parts of the human body.

11. A device according to claim 10, wherein the heat output and heat output difference generated in the human body by biochemical and chemical processes is recordable.

12. A device according to claim 10, wherein the heat generated by burning and oxidation of glucose, fatty acids, etc. is one of separately measurable according to the source and not separately measurable.

13. A device according to claim 10, wherein said at least one sensor head is a miniaturized device.

14. A device according to claim 10, wherein said at least one sensor head contains at least one miniaturized thermoelement or an integrated unit of several thermoelements.

15. A device according to claim 10, wherein said selectively detects at least one of thermal radiation and thermal conductivity.

16. A device according to claim 10, wherein said sensor head contains one or more temperature measuring devices, which are positioned geometrically in said sensor head in such a manner that said temperature measuring devices detect the heat issued by the body by thermal radiation, thermal conductivity and convection using one of contactless measurement and contacting measurement.

17. A device according to claim 10, wherein temperature or thermal output is selectively measured.

18. A device according to claim 10, wherein more than two temperature measuring devices are provided, of which a first one is provided for measuring thermal radiation, a second one for detecting contact heat, and a third temperature measurement device being placed very close to the first one, without being exposed to thermal radiation.

19. A device according to claim 10, wherein one or more temperature measuring devices are accommodated in one or more sensor heads in any random arrangement.

20. A device according to claim 19, wherein said sensor heads measure the heat in a contactless manner in the form of thermal radiation and/or with the object to be measured.

21. A device according to claim 10, wherein the entire electronic device is miniaturized.

22. A device according to claim 10, wherein said sensor head repeatedly detects the heat radiated from the defined area sections of the human body.

23. A device according to claim 10, wherein said sensor head has an opening and thereby is placeable on a defined area of the body in a reproducible manner within a prescribed tolerance.

24. A device according to claim 10, wherein said sensor head is made of a material or a combination of materials having a suitable thermal conductivity value.

25. A device according to claim 10, wherein said sensor head is made of wood having a suitable thermal conductivity value.

26. A device according to claim 10, wherein said sensor head is designed in the shape of a thermal radiation integrating hollow body such as an Ulbricht globe.

27. A device according to claim 10, wherein said sensor head is spatially separate from the electronic unit, measurement unit and output unit.

28. A device according to claim 10, wherein a hollow body of said sensor head contains at least one opening for the purpose of cooling.

29. A device according to claim 10, wherein a hollow body of said sensor head having an inert gas flowing through or being evacuated.

30. A device according to claim 28, wherein a device for measuring heat is provided next to said opening.

31. A device according to claim 28, wherein the device composed of various materials for contact measurement being disposed ring-like or in any irregular form around the opening.

32. A device according to claim 10, wherein said at least one NTC resistance is placed at the same distance, at different distances, offset or at an angle to each other of said at least one NTC resistance or in any irregular geometric arrangement.

33. A device according to claim 10, wherein at least one filter, a step filter or a set of filters of defined size are provided between the human body and said temperature measuring devices.

34. A device according to claim 33, wherein said filter, step filter or set of filters absorb, reflect or are impermeable within certain waverlength ranges.

35. A device according to claim 10, wherein said temperature measuring devices are located at a certain distance between 0 and 50 cm from the surface of the human body.

36. A device for non-invasive determination of glucose concentrations in parts of the human body using temperature measurement and heat detection, comprising:

at least one sensor head containing at least one NTC resistance for detecting heat from the human body;

an associated electronic control unit for converting analog measured values into digital data;

a measurement unit for measuring the heat detected by the at least one NTC resistance;

an evaluation unit for storing an algorithm and for applying said algorithm to output signals of said measurement unit to determine information depicting glucose concentrations in the human body; and an output unit coupled to the at least one sensor head for displaying said information depicting glucose concentrations in the human body.

* * * * *